United States Patent
Burke et al.

(10) Patent No.: US 9,943,445 B2
(45) Date of Patent: Apr. 17, 2018

(54) ANGULARLY ADJUSTABLE DEVICE FOR STABILIZING IMPALED OBJECTS IN THE HUMAN BODY

(71) Applicants: Ryan Burke, Great Falls, MT (US);
Joel Switzer, Bozeman, MT (US);
Stephen Sanford, Bozeman, MT (US);
David Yakos, Bozeman, MT (US)

(72) Inventors: Ryan Burke, Great Falls, MT (US);
Joel Switzer, Bozeman, MT (US);
Stephen Sanford, Bozeman, MT (US);
David Yakos, Bozeman, MT (US)

(*) Notice: Subject to any disclaimer, the term of this patent is extended or adjusted under 35 U.S.C. 154(b) by 353 days.

(21) Appl. No.: 14/866,114

(22) Filed: Sep. 25, 2015

(65) Prior Publication Data

US 2017/0087026 A1    Mar. 30, 2017

(51) Int. Cl.
*A61F 13/00*    (2006.01)
*A61M 16/04*    (2006.01)

(52) U.S. Cl.
CPC .......... *A61F 13/00051* (2013.01); *A61F 2013/00412* (2013.01); *A61M 16/0497* (2013.01)

(58) Field of Classification Search
CPC .... A61F 5/05; A61F 5/05825; A61F 5/05866; A61F 5/05875; A61F 5/08; A61F 5/10; A61F 5/37; A61F 2012/00412; A61F 13/10; A61F 13/104; A61F 13/105; A61F 2013/00412; A61M 16/0497
USPC .......... 128/852, 869, 877, 879, 880, 207.17; 602/12, 21, 22
See application file for complete search history.

(56) References Cited

U.S. PATENT DOCUMENTS

| | | | |
|---|---|---|---|
| 3,760,811 A | 9/1973 | Andrew | |
| 4,327,716 A | 5/1982 | Ansted | |
| 4,333,468 A * | 6/1982 | Geist | A61M 25/02 128/DIG. 26 |
| 5,232,453 A * | 8/1993 | Plass | A61M 25/02 128/DIG. 26 |
| 5,261,893 A * | 11/1993 | Zamierowski | A61F 5/453 128/DIG. 26 |
| 5,352,211 A * | 10/1994 | Merskelly | A61M 25/02 128/DIG. 26 |
| 5,375,588 A * | 12/1994 | Yoon | A61B 17/3403 600/114 |
| 5,478,333 A | 12/1995 | Asherman, Jr. | |
| 5,807,341 A * | 9/1998 | Heim | A61M 25/02 604/174 |
| 6,913,582 B2 * | 7/2005 | Chen | A61F 5/05866 128/878 |
| 7,413,561 B2 * | 8/2008 | Raulerson | A61M 25/02 604/174 |

(Continued)

*Primary Examiner* — Keri J Nelson
(74) *Attorney, Agent, or Firm* — Antoinette M. Tease

(57) ABSTRACT

A device for stabilizing impaled objects in the human body, the device having a first and a second component each of which is comprised of a generally T-shaped support plate that is adhered to a generally T-shaped foam pad. Each component has a lower section and a base section. The support plate comprises a bend line between the tower section and the base section and a channel along each outside edge of that portion of the support, plate that comprises the tower section. The foam pad comprises a slit along each, outside edge of that portion of the foam pad that comprises the tower section. First and second fastening straps are bonded between the support plates and foam pads.

6 Claims, 5 Drawing Sheets

(56) References Cited

U.S. PATENT DOCUMENTS

| | | |
|---|---|---|
| 8,636,763 B2 | 1/2014 | Lebner |
| 2005/0021083 A1 | 1/2005 | Lebner |
| 2008/0103451 A1* | 5/2008 | Schaefer, Jr. ......... A61F 13/022 |
| | | 604/180 |

* cited by examiner

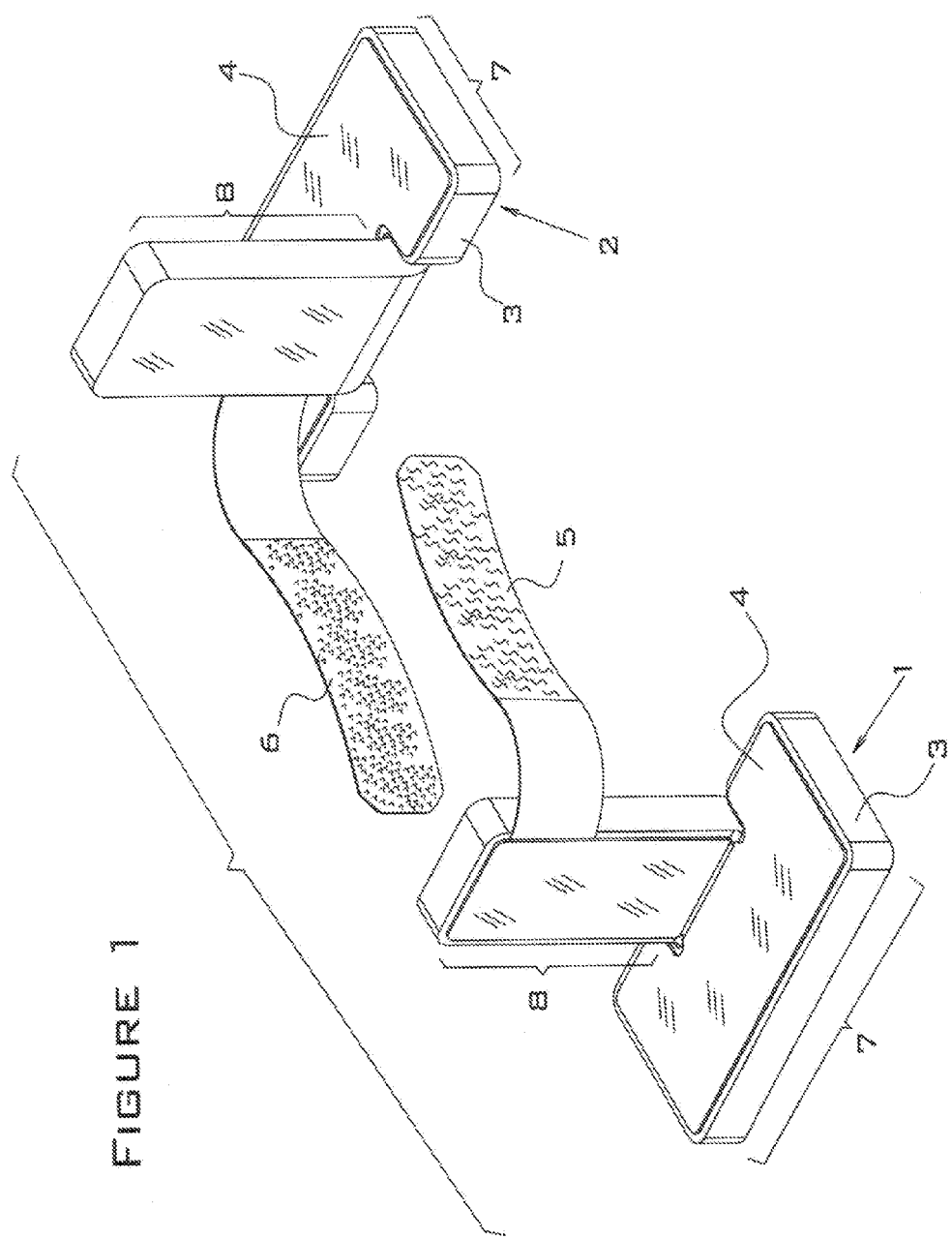

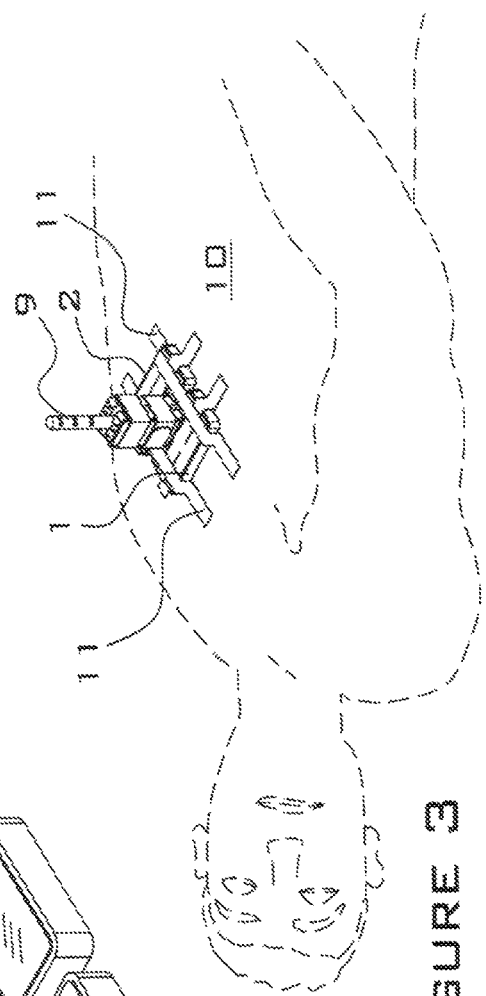
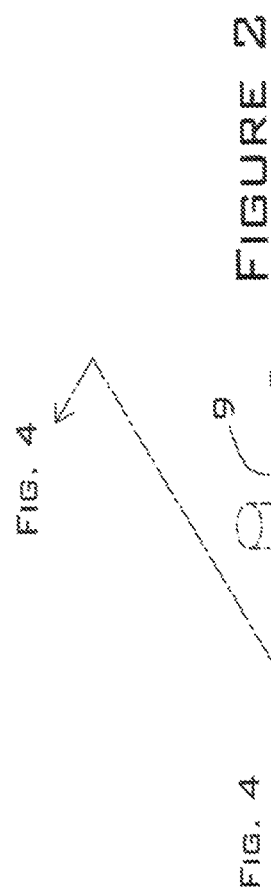

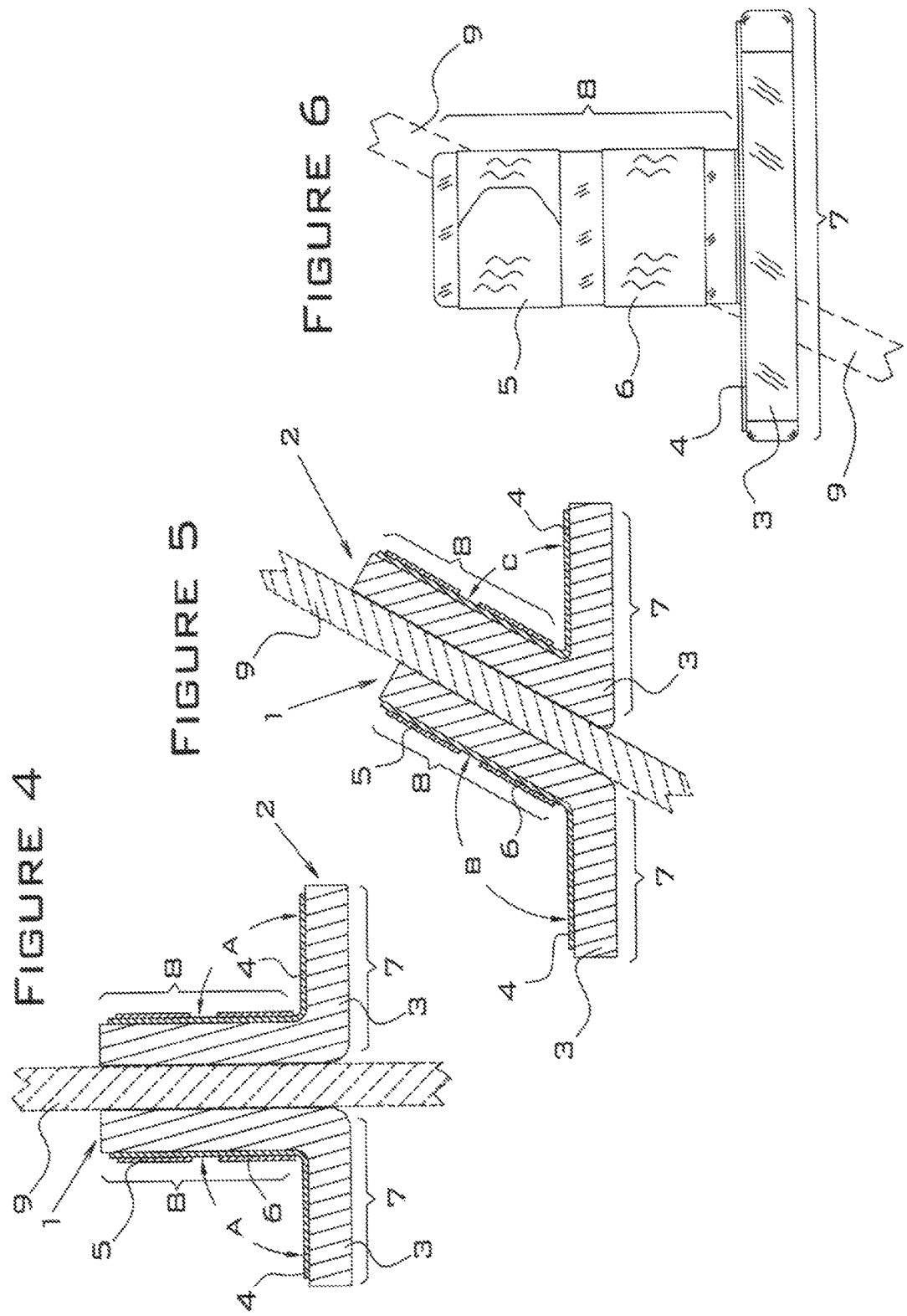

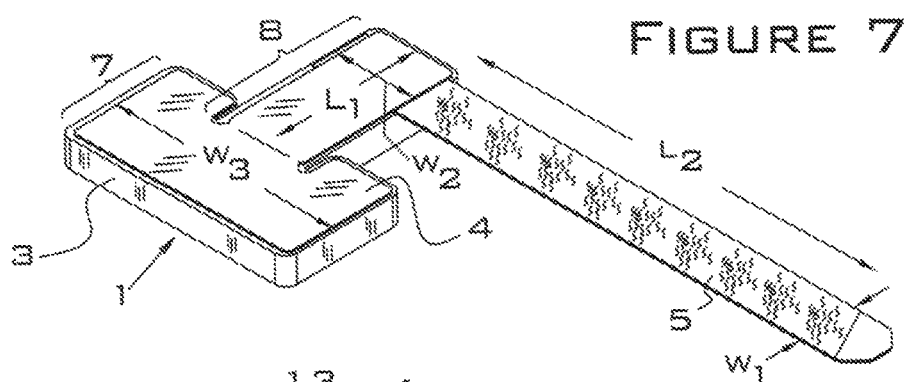
FIGURE 7
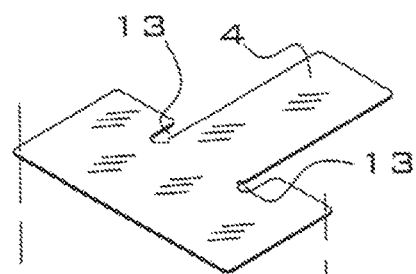
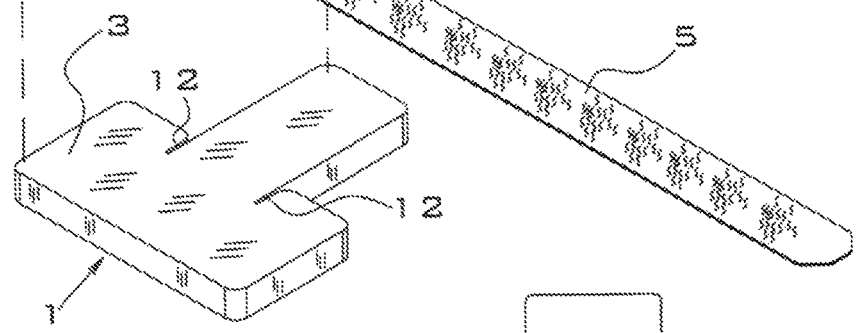
FIGURE 8
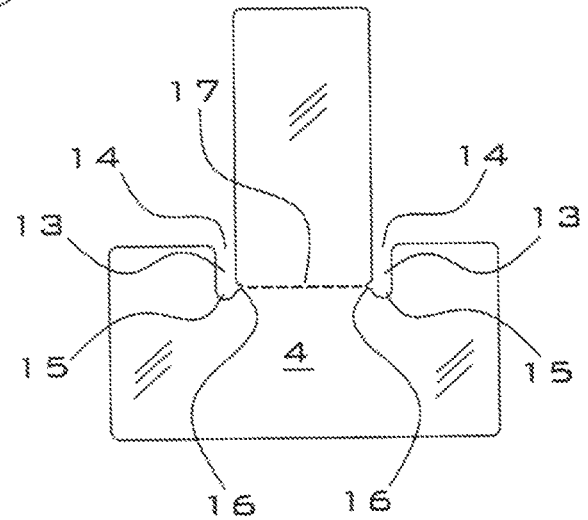
FIGURE 9

ANGULARLY ADJUSTABLE DEVICE FOR STABILIZING IMPALED OBJECTS IN THE HUMAN BODY

BACKGROUND OF THE INVENTION

1. Field of the Invention

The present invention, relates to the field of emergency treatment devices that stabilize impaled objects that protrude from the human body, and more particularly, to devices that are adjustable to match the angle of the protruding object, while also providing a degree of direct pressure to the wound area surrounding the protruding object.

2. Description of the Related Art

U.S. Pat. No. 3,760,811 (Andrew, 1973) discloses an endotracheal tube clamp that comprises a pair of wafer-shaped clamping members that lock together wife matching sawtooth protrusions. The device m manufactured from molded plastic and is removed from an endotracheal tube after use by breaking apart one of the two wafer-shaped members. The device does not incorporate adjustment for different diameters of tube, nor does it incorporate adjustment for tubes protruding from a patient's body at various angles.

U.S. Pat. No. 4,327,716 (Ansted, 1982) discloses an emergency stabilizer for objects such as ski poles, arrows, and industrial objects that have been accidently impaled in the human body. The device comprises a base pad that fits against the side of the body opposite to the protruding object, a plurality of circular pads with clefts that fit around the shaft of the protruding object, and a set of straps with hook-and-loop fasteners attached to the base that wrap around the invention and secure the circular pads in place around the protruding object. Unlike the present invention, this device does not comprise adjustable-angle metal supports to stabilize impaled objects that protrude non-perpendicularly from the plane of the accident victim's body. Furthermore, this device is impractical, bulky and difficult to use.

U.S. Pat. No. 5,478,333 (Ashemutn, Jr., 1995) discloses a medical dressing used by first responded for treating open chest injuries. This device comprises a one-way valve with an adhesive backing that is placed over a chest wound so as to prevent the entry of outside air into the chest cavity, while allowing trapped internal air and blood to exit the chest cavity. This invention is not designed to stabilize objects that protrude from a wound.

U.S. Pat. No. 8,636,763 (Lebner 2014) discloses a device for closing lacerations or incisions. The device consists of two pieces manufactured from polymeric film. During use, one of the two pieces is bonded to each side of a wound by adhesive, and the two pieces are then bonded together with additional adhesive. This invention is not designed to stabilize objects that protrude from a wound.

BRIEF SUMMARY OF THE INVENTION

The present invention is a device for stabilizing impaled objects in the human body comprising: a first component comprising a first foam pad, a first support plate, a first fastening strap, a first substantially rectangular base section, and a first substantially rectangular tower section, the first fastening strap being comprised of hook-and-loop material and connected to an upper half of the first tower section, the first support plate being comprised of a material having ductility and stiffness, the first foam pad being substantially T-shaped and the first support plate being substantially T-shaped, the first support plate being boned to a top surface of the first foam pad, and the first fastening strap being bonded between the first foam pad and the first support plate; a second component comprising a second foam pad, a second support plate, a second fastening strap, a second substantially rectangular base section, and a second substantially rectangular tower section, the second fastening strap being comprised of a hook-and-loop material and connected to a lower half of the second tower section, the second support plate being comprised of a material having ductility and stiffness, the second foam pad being substantially T-shaped and the second support plate being substantially T-shaped, the second support plate being bonded to a top surface of the second foam pad, and the second fastening step being bonded between the second foam pad and the second support plate; wherein the first lower section comprises a first portion of the first foam pad and a first portion of the first support plate, wherein the second tower section comprises a first portion of the second foam, pad and a first portion of the second support plate, wherein the first and second tower sections each has a length, wherein each of the first and second fastening straps has a width, and wherein the length of the first tower section is at least equal to a sum of the widths of the first and second fastening straps and the length of the second tower section is at least equal to the sum of the widths of the first and second fastening straps; and wherein the first base section comprises a second portion of the first foam pad and a second portion of the first support plate, wherein the second base section comprises a second portion of the second foam pad and a second portion of the second support plate, wherein the first and second base sections each has a width, wherein the first tower section is centered along the width of the first base section and the second tower section is centered along the width of the second base section.

In a preferred embodiment, each of the first and second foam pads and the first and second support plates has rounded corners. Preferably, the first and second fastening straps each has a length, the first and second tower sections each has a width, the length of the first fastening strap is at least six times greater than the width of the first tower section, and the length of the second fastening strap is at least six times greater than the width of the second tower section. Preferably, the first and second base sections each has a width, the first and second tower sections each has a width, the width of the first base section is between two and three times the width of the first tower section, and the width of the second base section is between two and three times the width of the second tower section.

In a preferred embodiment, the first and second foam pads each has a thickness, the first and second support plates each has a thickness, aid the thickness of the first foam pad is approximately sixteen times greater than the thickness of the first support plate, and the thickness of the second foam pad is approximately sixteen times greater than the thickness of the second support plate. Preferably, the first support plate comprises a first channel along a first outside edge of the first portion of the first support plate that comprises the first tower section, the first channel extends into the second portion of the first support plate that comprises the first base section, the first support plate comprises a second channel along a second outside edge of the first portion of the first support plate that comprises the first tower section, the second channel extends into the second portion of the first support plate that comprises the first base section; and the second support plate comprises a third channel along a first outside edge of the first portion of the second support plate that comprises the second tower section, the third channel extends into tire second portion of the second support plate that comprises the second base section, the second support plate comprises a fourth channel along a second outside edge of the first portion of the second support plate that comprises the second tower section, and the fourth channel extends into the second portion of the second support plate that comprises the second base section.

In a preferred embodiment, the first and second channels each has a length, the first base section has a length, the length of the first and second channels is each approximately one-third of the length of the first base section, the third and fourth channels each has a length, the second base section has a length, and the length of the third and fourth channels is each approximately one-third of the length of the second base section. Preferably, the first foam pad comprises a first slit along a first outside edge of the first portion of the first foam pad that comprises the first tower section, the first slit extends into the second portion of the first foam pad that comprises the first base section, the first foam pad comprises a second slit along a second outside edge of the first portion of the first foam pad that comprises the first tower section, and the second slit extends into the second portion of the first foam pad that comprises the first base section; and the second foam pad comprises a third slit along a first outside edge of the first portion of the second foam pad that comprises the second tower section, the third slit extends into the second portion of the second foam pad that comprises the second base section, the second foam pad comprises a fourth slit along a second outside edge of the first portion of the second foam pad that comprises the second tower section, and the fourth slit extends into the second portion of the second foam pad that comprises the second base section.

In a preferred embodiment, the first and second slits each has a length, the first base section, has a length, and the length of the first and second slits is each approximately one-fourth of the length of the first base section, the third and fourth slits each has a length, the second base section has a length, and the length of the third and fourth slits is each approximately one-fourth of the length of the second base section. Preferably, each of the first, second, third and fourth channels comprises an open end and a rounded end. Preferably, each rounded end of the first and second channels is semicircular in shape with a notch that extends from the rounded end toward a first bend line in the first support plate, the first bend line has two ends, the rounded ends of the first and second channels are located on an interior side of either end of the first bend line; and each rounded end of the third and fourth channels is semicircular in shape with a notch that extends from the rounded end toward a second bend line in the second support plate, the second bend line has two ends, and the rounded ends of the third and fourth channels are located on an interior side of either end of the second bend line.

BRIEF DESCRIPTION OF DRAWINGS

FIG. 1 is an isometric view of the present invention, showing the first component and the second component separated and in upright positions.

FIG. 2 is an isometric view of the present invention, showing the first component and the second component secured around a protruding impaled object.

FIG. 3 is an isometric view of the present invention shown attached to an accident victim who has a protruding impaled-object injury.

FIG. 4 is a side cross-section view of the present invention, shown stabilizing an impaled object that protrudes in a direction perpendicular to the surface plane of an accident victim's body.

FIG. 5 is a side cross-section view of a first installation configuration of the present invention, shown stabilizing an impaled object that protrudes at a non-perpendicular angle from the plane of an accident victim's body.

FIG. 6 is a side view of a second installation configuration of the present invention, shown stabilizing an impaled object that protrudes at a non-perpendicular angle from the plane of an accident victim's body.

FIG. 7 is an isometric view of die first component, shown in the shape in which it is manufactured and packaged.

FIG. 8 is an exploded isometric view of the first component that is shown in FIG. 7, further illustrating the shapes and relative positions of the foam pad, the support plate, and the first fastening strap.

FIG. 9 is a fop view of a support plate, shown in a flat, as-manufactured configuration.

REFERENCE NUMBERS

Figure 10:
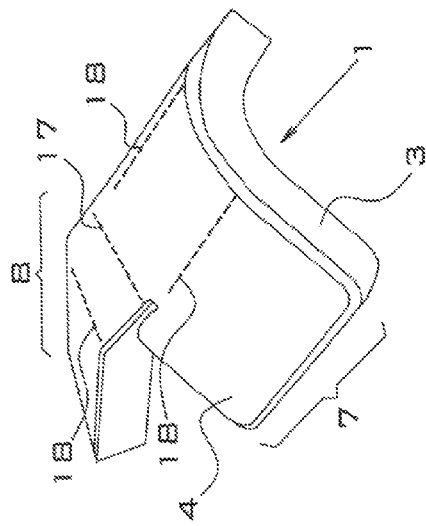
FIG. 10 is a perspective view of the first component, shown with the base section and the tower section slightly bent so as to form a generally three-dimensional convex (i.e., cup-shaped or arched) structure.

1 First component
2 Second component
3 Foam pad
4 Support plate
5 first fastening strap
6 Second fastening strap
7 Base section
8 Tower section
9 Impaled object
10 Accident victim
11 Medical tape
12 Slit (in foam pad)
13 Channel tin support plate)
14 Open end of channel
15 Rounded end of channel
16 Notch within rounded end of channel
17 Primary bend line (of support plate)
18 Secondary bend lines (of support plate)

DETAILED DESCRIPTION OF INVENTION

The present invention is an emergency medical device that is designed to support and stabilize impaled objects that are protruding from the body of an accident victim until the victim can be transported to a medical facility for treatment. Standard procedure in emergency medicine is not to remove, and to limit movement of, impaled objects anywhere in the body unless it is obstructing an airway. The present invention is a two-piece device that clamps around the impaled object and also attaches to the body of the victim. The present invention is designed to be used with most small and medium impaled object injuries to the body. In an alternate application, one of the two pieces of the invention may be used singly to serve as a protective cover over a non-protruding foreign object or body injury. The present invention is useful for a variety of potential applications, including, but not limited to, military or battlefield operations, falls, assaults with weapons, back country accidents, automobile, boat, snowmobile and ATV crashes, and construction site accidents. Examples of small- to medium-sized impaled objects that may be stabilized with the present invention include, but are not limited to, shrapnel, knives, arrows, ski poles, tree branches, pencils, pens, scissors, glass shards, and automobile crash debris.

FIG. 1 is an isometric view of the present, invention. The present invention is comprised of a first component 1 and a second component 2, which are shown separated and in upright positions, such as immediately before the present invention is installed around an impaled object. The first component 1 and the second component 2 each comprises a foam pad 3 and a support, plate 4. The first component 1 comprises a first fastening strap 5, and the second component 2 comprises a second fastening strap 6. The first component 1 and the second component 2 each comprise a substantially rectangular and horizontal base section and a substantially rectangular tower section 8. Each of the base sections and each of the tower sections 8 comprises a portion of a foam pad 3 and a portion of a support plate 4. The tower sections 8 may be positioned at any angle between horizontal and vertical, as described in more detail with reference to FIGS. 4 through 6. The first fastening strap 5 of the first component 1 is connected to the upper half of the tower section 8 of the first component 1, and the second fastening snap 6 of the second, component 2 is connected to the lower half of the tower section 8 of the second component 2, as shown in FIG. 1. The first component 1 and the second component 2 are similar except for the positions of the first fastening strap 5 and the second fastening strap 6 on their respective tower sections 8. As shown, the fastening strap 5 of the first component 1 is wrapped around the tower section 8 of the second component 2, and the fastening strap 6 of the second component 2 is wrapped around the tower section 8 of the first component 1. Alternately, medical tape may be used in lieu of the fastening straps 5, 6 to secure the two tower sections 8 together.

The foam pads 3 are each preferably manufactured from a single piece of ½-inch thick, open-cell polymer foam. The support plates 4 are each preferably manufactured from a single piece of 20-gauge aluminum alloy plate, for example. Series 3003, temper H14 aluminum alloy. The first fastening strap 5 and the second fastening strap 6 are preferably hook-and-loop type (e.g., VELCRO™) fasteners, with hooks on one side and loops on the opposite side of each strap.

The assembly methods of the various components of the present invention are described in reference to FIGS. 7 and 8. Although the present invention may be manufactured in any size. In a preferred embodiment, the base sections 7 have a length of about 2.2 inches and a width of about 4.2 inches, and the tower sections 8 have a width of about 1.6 inches and a length of about 2.5 inches.

FIG. 2 is an isometric view of the present invention shown with the first component 1 and the second component 2 secured around a protruding impaled object 9 (for example, an arrow shaft). As shown, the first fastening strap 5 and the second fastening strap 6 wrap around the two tower sections 8, thereby holding the two tower sections 8 in contact with the impaled object 9, and the portions of the foam pads 3 that are in contact with the outside surface of the impaled object 9 compress slightly so as to form a snug fit around the impaled object 9. With the present invention secured to the impaled object 9 as shown, the position of the impaled object 9 is fixed and prevented from movement relative to the present invention.

FIG. 3 is an isometric view of the present invention being used for emergency treatment of an accident victim 10 having a protruding impaled-object injury. As shown, the first component 1 and the second component 2 are secured in place around the impaled object 9 as described previously in reference to FIG. 2. The present invention is secured to the chest of the accident victim 10 with medical tape 11, which fixes the position of the present invention relative to the body of the accident victim 10. It should be noted the present invention may be used on any part of the body, including, but not limited to, the chest, back, neck, a limb, or the head. With the impaled object 9 secured to the present invention and the present invention secured to the accident victim 10 as shown, the impaled object 9 is prevented from moving relative to the accident victim's body in any direction, including the longitudinal (in and out), axial (back and forth) and rotational directions. In addition to stabilizing the impaled object the present invention can also assist with applying a degree of direct pressure to the victim's body area around the impaled object, thereby helping to reduce bleeding from the wound and tissue swelling from around the wound, while also protesting the injured zone from further microbial contamination.

FIGS. 4, 5 and 6 illustrate the ability of the present invention to support impaled objects that protrude from any angle from an accident victim's body. FIG. 4 is a side cross-section vie w of the present invention taken at the section line shown in FIG. 2. FIG. 4 illustrates the present invention used to support an impaled object 9 that protrudes in a direction perpendicular to the surface plane of the accident victim's body, in this example, the tower section 8 of the first component 1 and the tower section 8 of the second component 2 have each been bent to form an angle A with respect to the base sections 7, with the angle A being ninety (90) degrees.

FIG. 5 is a side cross-section view of a first installation configuration of the present invention being used to support, an impaled object 9 that protrudes at a non-perpendicular angle from the plane of the accident victim's body. In this example, the tower section 8 of the first component 1 is bent at an obtuse angle B with respect to the base section 7, and the tower section 8 of the second component 2 is bent at an acute angle C with respect to the base section 7, with the sum of the angles B and C equal to one hundred eighty (180) degrees.

FIG. 6 is a side view of a second installation configuration of the present invention being used to support, an impaled object that protrudes at a non-perpendicular angle from the plane of the accident victim's body, in this configuration, the two towers B are each bent to angles of ninety (90) degrees with respect to the base sections 7, as shown in FIG. 4, and then the present invention is attached to the impaled object 9 so that the impaled object 9 is positioned diagonally between the two towers 8.

The dimensions and material type of the support plates 4 of the present invention are selected so that the support plates 4 have sufficient ductility to be bent to any desired angle and sufficient stiffness so that the tower sections 8 of the present invention remain at their desired angular positions when the present invention is attached to an impaled object 9.

FIG. 7 is m isometric view of the first component 1, shown in the shape in which it is manufactured and packaged. As shown, in the as-manufactured state, the first component 1 comprises a flat, generally T-shaped foam pad 3, a flat, generally T-shaped support plate 4 that is bonded with adhesive to the top surface of the foam pad 3, and a flat first fastening strap 5 that is bonded with adhesive between the foam pad 3 and the support plate 4. The corners of the foam pad 3, the support plate 4 and the first fastening strap 5 are preferably rounded to eliminate sharp edges that might injure the skin of an accident victim. The length $L_1$ of the tower section 8 is preferably at least twice the width $W_1$ of the first fastening strap 5 so that the first fastening strap 5 and the second fastening strap 6 may fee simultaneously wrapped around the tower sections 8 of the first component 1 and the second component 2, with the first fastening strap 5 positioned above the second fastening strap 6, as shown in FIG. 2. The length $L_2$ of the first fastening strap 5 is preferably at least 6 times greater than the width $W_2$ of the tower section 8 so that the first fastening strap 5 is sufficiently long to wrap around the tower sections 8 of the first component 1 and the second component 2 when the two tower sections 8 are supporting a protruding impaled object, as shown in FIGS. 2 and 3.

The tower section 8 is preferably centered along the width $W_3$ of the base section 7. The width $W_3$ of the base section 7 is preferably about 2.6 times (between two and three times) greater than the width $W_2$ of the tower section 8, thereby providing sufficient horizontal top surface area on the base section 7 for attaching the present invention to an accident victim 10 with medical tape 11, as shown in FIG. 3. The thickness of the foam pad 3 is preferably about 16 times greater than the thickness of the support plate 4, thereby providing adequate compressibility and liquid absorption capacity of the foam pad 3 along with adequate rigidity of the support plate 4.

As previously described, the second component 2 (shown in FIGS. 1 through 5) is constructed identically to the first component 1, except that the positions of the first fastening strap 5 and the second fastening strap 6 in relation to their respective tower sections 8 are different. Preferably, the first component 1 and the second component 2 are sterilized and sealed in sterile packaging alter manufacture.

FIG. 8 is an exploded isometric view of the first component 1 that is shown in FIG. 7, further illustrating the shapes and relative positions of the foam pad 3, the support plate 4, and the first fastening strap 5. The foam pad 3 comprises a slit 12 along each outside edge of that portion of the foam pad 3 that comprises the tower section 8 shown in FIG. 7, with each slit 12 extending into that portion of the loans pad 3 that comprises the base section 7 shown in FIG. 7, and with the silt length approximately one-fourth (¼) of the length of the base section 7.

The support plate 4 comprises a channel 13 along each outside edge of that portion of the support plate 4 that comprises the tower section 8 shown in FIG. 7, with each channel 13 extending into that portion of the support plate 4 that comprises the base section 7 shown in FIG. 7, and with the channel length 13 approximately one-third of (⅓) the length of the base section 7. The width of each channel 13 is approximately 4.3 times greater than the width of one of the slits 12, and the length of each channel 13 is approximately 1.2 times greater than the length of one of the slits 12. The slits 12 and the channels 13 allow the first component 1 and the second component 2 to be positioned more closely together than would be possible without the slits 12 and the channels 13 when the present invention is attached to a protruding impaled object 9, as shown in FIG. 2, thereby maximizing the support that is provided to the impaled object 9 by the present invention.

The foam pads 3 and support plates 4 are preferably manufactured by stamping or cutting and are compatible with mass manufacturing processes. The fastening straps 5 (and identical fastening straps 6, not shown) are preferably obtained as pre-manufactured commercial items, for example, part number 9402T61 from McMaster-Carr Supply Company of Santa Fe Springs, Calif.

FIG. 9 is a top view of a support plate 4, shown in a flat, as-manufactured configuration. As shown, each channel 13 comprises an open end 14 and a rounded end 15. Each rounded end 15 is generally semicircular in shape with a notch 16 that extends from the rounded, end 15 inward toward the bend line 17 (to facilitate bending at the primary bend line 17). The support plate 4 is designed to bend along a primary bend line 17 when the tower section 8 of the present invention is bent upward, as shown in FIGS. 1 through 6. The rounded ends 15 of the channels 13 are located on the interior side of either end of the primary bend fine 17. The presence of the rounded ends 15 serves to eliminate sharp corners, thereby minimizing local stresses in the support plate 4 at the primary bend line 17 and preventing stress cracks from forming in the support plate 4 when the present invention is bent into position for installation around an impaled object.

Figure 12:
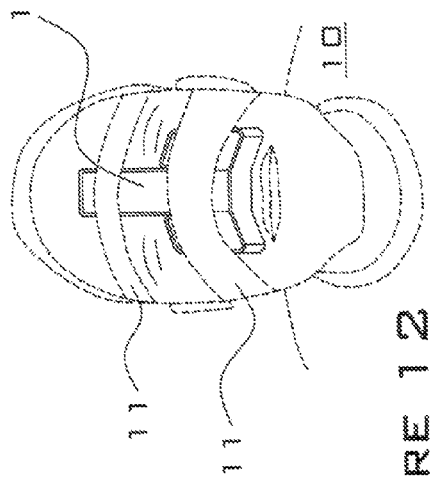
FIG. 12 is a front view of an accident victim shown with a first component of the present invention used to cover the accident victim's broken nose.
Figure 11:
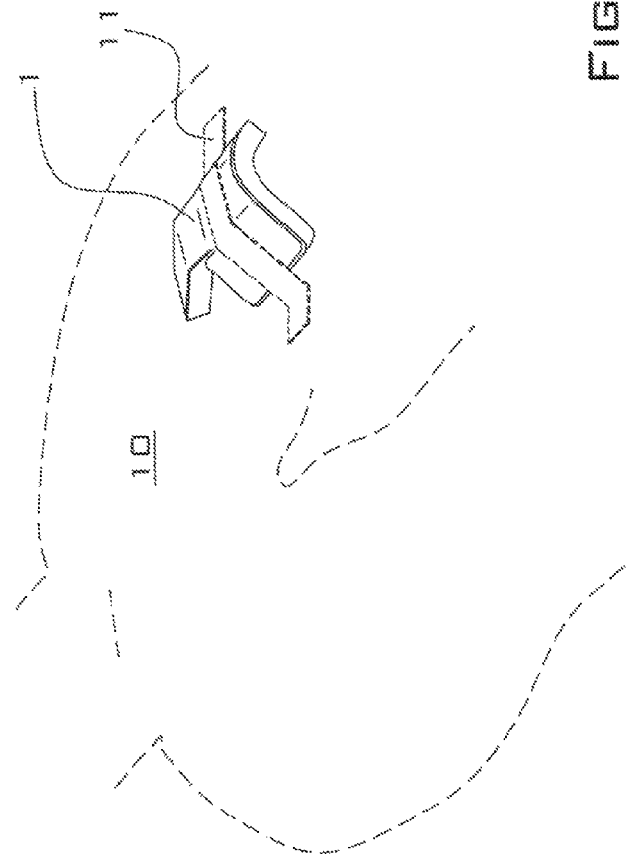
FIG. 11 is a perspective view of an accident victim with a first component of the present invention shown covering an impaled object that is either not protruding, or only slightly protruding, from the accident victim's chest.

FIGS. 10 through 12 describe an alternate method for employing the present invention, in which only one of the first component 1 or the second component 2 is utilized singly for emergency treatment of an accident victim. FIG. 10 is a perspective view of the first component 1 that has had the first fastening strap 5 (shown in FIGS. 1 through 8) removed (for example, by clipping with medical shears). As shown, the base section 7 and the rower section 8 are slightly bent along the primary bend line 17 and along secondary bend lines 18 so that the first component 1 forms a generally three-dimensional convex (i.e., cup-shaped or arched) structure. This shape is useful to provide a protective emergency covering for injuries that do not require the present invention to be physically connected to a protruding impaled object. Examples of these types of injuries are described in reference to FIGS. 11 and 12.

FIG. 11 is a perspective view of an accident victim 10 with a first component 1 of the present invention used to cover an impaled object (not shown) that is not protruding, or only slightly protruding, from the accident victim's chest in this application, the first component 1 is bent to a required shape so that it does not contact the impaled object but instead forms a protective arch-shaped covering to prevent foreign objects from touching the impaled object as the accident victim 10 is transported to a medical facility. As shown, the first component 1 is held in place with a strip of medical tape 11 that is attached to the accident victim's skin. Multiple strips of medical tape 11 may be used as necessary to secure the first component 1.

FIG. 12 is a front view of an accident victim 10 with a first component 1 of the present invention used to cover a broken nose. In this application, the first component 1 is bent to a required shape so that it does not contact the broken nose or surrounding area but instead forms a protective covering to prevent foreign objects from touching the injured area as the accident victim 10 is transported to a medical facility. As shown, the first component 1 is held in place with strips of medical tape 11 that are attached to or around the accident victim's face.

The porosity and permeability of the open-cell material of the foam pads 3 of the present invention provide the foam pads with flexibility and an ability to absorb blood, and other fluids. In addition to use as an emergency field device, the present invention may be used to stabilize chest tubes and other protruding objects while a patient is moved within a treatment facility.

Although, in most cases, protruding impaled objects are best stabilized by using both the first component 1 and the second component 2 together, as described in reference to FIGS. 1 through 6, in some eases it may be better to use only one of the components alone to attach to and stabilize a protruding impaled object. The present invention may be trimmed to a smaller size or specific shape as required for a particular application using trauma shears. The present invention may be attached to the body of an accident victim with trauma wraps (for example, COBAN™ or KER-LEX™) rather than, or in addition to, medical tape.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A device for stabilizing impaled objects in the human body comprising:
    (a) a first component comprising a first foam pad, a first support plate, a first fastening strap, a first substantially rectangular base section, and a first substantially rectangular tower section, the first fastening strap being comprised of hook-and-loop material and connected to an upper half of the first tower section, the first support plate being comprised of a material having ductility and stiffness, the first foam pad being substantially T-shaped and the first support plate being substantially T-shaped, the first support plate being bonded to a top surface of the first foam pad, and the first fastening strap being bonded between the first foam pad and the first support plate;
    (b) a second component comprising a second foam pad, a second support plate, a second fastening strap, a second substantially rectangular base section, and a second substantially rectangular tower section, the second fastening strap being comprised of a hook-and-loop material and connected to a lower half of the second tower section, the second support plate being comprised of a material having ductility and stiffness, the second foam pad being substantially T-shaped and the second support plate being substantially T-shaped, the second support plate being bonded to a top surface of the second foam pad, and the second fastening strap being bonded between the second foam pad and the second support plate;
    wherein the first tower section comprises a first portion of the first foam pad and a first portion of the first support plate, wherein the second tower section comprises a first portion of the second foam pad and a first portion of the second support plate, wherein the first and second tower sections each has a length, wherein each of the first and second fastening straps has a width, and wherein the length of the first tower section is at least equal to a sum of the widths of the first and second fastening straps and the length of the second tower section is at least equal to the sum of the widths of the first and second fastening straps; and
    wherein the first base section comprises a second portion of the first foam pad and a second portion of the first support plate, wherein the second base section comprises a second portion of the second foam pad and a second portion of the second support plate, wherein the first and second base sections each has a width, wherein the first tower section is centered along the width of the first base section and the second tower section is centered along the width of the second base section;
    wherein the first support plate comprises a first channel along a first outside edge of the first portion of the first support plate that comprises the first tower section, wherein the first channel extends into the second portion of the first support plate that comprises the first base section, wherein the first support plate comprises a second channel along a second outside edge of the first portion of the first support plate that comprises the first tower section, wherein the second channel extends into the second portion of the first support plate that comprises the first base section; and
    wherein the second support plate comprises a third channel along a first outside edge of the first portion of the second support plate that comprises the second tower section, wherein the third channel extends into the second portion of the second support plate that comprises the second base section, wherein the second support plate comprises a fourth channel along a second outside edge of the first portion of the second support plate that comprises the second tower section, wherein the fourth channel extends into the second portion of the second support plate that comprises the second base section.

2. The device of claim 1, wherein the first and second channels each has a length, wherein the first base section has a length, and wherein the length of the first and second channels is each approximately one-third of the length of the first base section, wherein the third and fourth channels each has a length, wherein the second base section has a length, and wherein the length of the third and fourth channels is each approximately one-third of the length of the second base section.

3. The device of claim 1, wherein the first foam pad comprises a first slit along a first outside edge of the first portion of the first foam pad that comprises the first tower section, wherein the first slit extends into the second portion of the first foam pad that comprises the first base section, wherein the first foam pad comprises a second slit along a second outside edge of the first portion of the first foam pad that comprises the first tower section, wherein the second slit extends into the second portion of the first foam pad that comprises the first base section; and
    wherein the second foam pad comprises a third slit along a first outside edge of the first portion of the second foam pad that comprises the second tower section, wherein the third slit extends into the second portion of the second foam pad that comprises the second base section, wherein the second foam pad comprises a fourth slit along a second outside edge of the first portion of the second foam pad that comprises the second tower section, wherein the fourth slit extends into the second portion of the second foam pad that comprises the second base section.

4. The device of claim 3, wherein the first and second slits each has a length, wherein the first base section has a length, and wherein the length of the first and second slits is each approximately one-fourth of the length of the first base section, wherein the third and fourth slits each has a length, wherein the second base section has a length, and wherein the length of the third and fourth slits is each approximately one-fourth of the length of the second base section.

5. The device of claim 1, wherein each of the first, second, third and fourth channels comprises an open end and a rounded end.

6. The device of claim 5, wherein each rounded end of the first and second channels is semicircular in shape with a notch that extends from the rounded end toward a first bend line in the first support plate, wherein the first bend line has two ends, wherein the rounded ends of the first and second channels are located on an interior side of either end of the first bend line; and wherein each rounded end of the third and fourth channels is semicircular in shape with a notch that extends from the rounded end toward a second bend line in the second support plate, wherein the second bend line has two ends, wherein the rounded ends of the third and fourth channels are located on an interior side of either end of the second bend line.

\* \* \* \* \*